(12) United States Patent
Colditz (10) Patent No.: US 8,337,441 B2
(45) Date of Patent: Dec. 25, 2012

(54) ADJUSTABLE MODULAR SPLINT SYSTEM

(76) Inventor: Judy C. Colditz, Raleigh, NC (US)

(*) Notice: Subject to any disclaimer, the term of this patent is extended or adjusted under 35 U.S.C. 154(b) by 0 days.

(21) Appl. No.: 12/868,156

(22) Filed: Aug. 25, 2010

(65) Prior Publication Data

US 2011/0054371 A1  Mar. 3, 2011

Related U.S. Application Data

(60) Provisional application No. 61/236,761, filed on Aug. 25, 2009.

(51) Int. Cl.
*A61F 5/00* (2006.01)

(52) U.S. Cl. .............................................. 602/21; 602/5

(58) Field of Classification Search .............. 602/21–22, 602/5; 128/878–880, 877; 24/70 ST
See application file for complete search history.

(56) References Cited

U.S. PATENT DOCUMENTS

| | | | |
|---|---|---|---|
| 4,602,620 A | 7/1986 | Marx | |
| 4,765,320 A | 8/1988 | Lindemann et al. | |
| 4,790,300 A | 12/1988 | Marx | |
| 5,544,877 A * | 8/1996 | Brownell | 473/450 |
| 5,643,186 A * | 7/1997 | Chinchalkar | 602/32 |
| 5,876,363 A | 3/1999 | Marx | |
| 6,651,352 B2 * | 11/2003 | McGorry et al. | 33/512 |
| 7,001,352 B2 * | 2/2006 | Farrell et al. | 602/21 |
| 7,311,686 B1 * | 12/2007 | Iglesias et al. | 602/20 |
| 7,390,057 B2 * | 6/2008 | Autterson | 296/214 |
| 2006/0084897 A1 * | 4/2006 | Duren et al. | 602/21 |
| 2007/0167893 A1 * | 7/2007 | Frisbie | 602/12 |

OTHER PUBLICATIONS

Pages from the 2009 Patterson Medical-Sammons Preston Hand Rehab catalogue.
Page from the 2007-2008 North Coast Medical catalogue.

* cited by examiner

*Primary Examiner* — Loan Thanh
*Assistant Examiner* — Camtu Nguyen
(74) *Attorney, Agent, or Firm* — Myers Bigel Sibley & Sajovec (57) ABSTRACT

A modular splint system having a base for securing to the limb, with various intervening components for joint positioning, with outriggers for mounting various tensioning devices and secured to the base with reclosable fasteners for precise alignment of forces.

12 Claims, 9 Drawing Sheets

ADJUSTABLE MODULAR SPLINT SYSTEM

RELATED APPLICATION

This application claims the benefit of and priority to U.S. Provisional Patent Application No. 61/236,761 filed Aug. 25, 2009 the disclosure of which is incorporated herein by reference.

BACKGROUND OF INVENTION

The human hand consists of a large number of bones and joints. Injuries to and diseases of the hand can upset the alignment of those bones and the articulation of the joints. The hand can be prone to adhesion and stiffness following immobilization. Therapeutic splints/orthoses are sometimes used to protect movement of the joints in the hand or to gain or maintain movement of those joints. The splint may also allow or control articulation of other joints, such as the wrist or elbow.

Therapeutic splints can be applied by a therapist or other trained individual to help the patient regain his/her normal functionality of the hand. These splints may have outriggers that carry hardware to control movement of loops carried by the fingers. The control may extend the fingers to counteract the tendency of the injured to flex the fingers or may flex the fingers or other joints. By movement of the fingers the range of motion is restored and/or preserved. Currently pre-molded splints/orthoses are available that hold a joint or joints in one position. These splints are one size and may fit in one area but be too large or small in another area. Some of these splints are made of fabric with metal stays which can be removed and adjusted. Other splints are available which can be bent to position an entire hand. For certain problems, the splint/orthosis base is custom molded using low temperature thermoplastic materials.

Currently many types of outrigger, hook and pulley parts are available. These components must be manually put together before being applied to the custom molded base. Additionally, they must be manually attached to the base with rivets, screws, or bonded between thermoplastic layers. This multiple level construct is time consuming and once the entire constructed component is applied it must be entirely removed and reapplied to adjust the location for the correct line of pull. This is very time consuming and challenging for those constructing such devices.

SUMMARY

Embodiments according to the invention disclosed herein relate to splinting and primarily hand/upper extremity splinting. Particularly they relate to a modular system where the splint can readily and rapidly be tailored to the patient's situation. Formable pre-molded modular base components are fitted to the patient's extremity, e.g. forearm, hand, etc. The base can be secured to the extremity by e.g. mounting straps. Modular components such as outriggers, hooks, pulleys, etc. can be readily and securely attached to a base. These components can be easily attached to the base at the appropriate positions and orientation consistent with the planned therapy and then can be easily secured in that location. Embodiments provide a one-unit attachable outrigger device that does not require construction.

This new system provides individually sized components, each of which can be bent to conform to the underlying shape and which can also be adjusted by modifying the edges. Straps can be positioned at a variety of positions and angles. Base components are connected with intervening components. As the multiple components of this system are assembled there is an opportunity for multiple adjustments which makes the system adaptable to both size and contour of the body part to which it is applied. These embodiments provide a splinting/orthotic system with a high level of adjustability for both size and fit without requiring a custom molded base.

This new system provides both intervening static components for precise positioning of the intervening joint and also moveable intervening components which allow precise joint movement. Some of the new intervening components are adjustable, allowing quick and easy repositioning of joint.

In some embodiments, the device may be applied anterior, posterior, medial or lateral or circumferentially around an extremity or extremity part (example: the thumb). In some embodiments, the base shape, size, contour and rigidity can vary. In some embodiments, the pre-molded base forms may be coupled with a strapping material. In some embodiments, the pre-molded base forms may be coupled with other intervening parts. In some embodiments, molded interlocking material such as a resealable fastener may be attached to one or more sides. In some embodiments, the base form may have a pre-molded edge contour which can accept a strap coupling component. In other embodiments, hook and loop fastener is optional. In some embodiments, the base form may or may not include a molded interlocking component on one or more surfaces.

The device may also include strapping components coupled with the base form and/or the outrigger component and/or loop component and/or intervening component. In some embodiments the strapping component may vary in shape, size, contour and length. In some embodiments, the strapping component may include a swivel attachment component. In some embodiments, the strapping component may have an adjustable length. In some embodiments, the strapping component may be coupled with a molded interlocking component of the base form, the outrigger component, and/or intervening components and/or hooks, pulleys, or hinge components for quick and secure connection. The strapping component can include a preformed shape that includes an adjustable and releasable part at one end and a moveable adjustable part at the opposing end with or without intervening components. In some embodiments, the strapping component may also be provided without the base unit to be applied to custom molded bases.

The advantages listed above culminate in a significant time savings when splints/orthoses need to be applied in a custom manner. The new system consists of choosing and assembling components, all of which inherently provide adjustability. This construction is significantly faster than molding a custom splint/brace base, applying straps and then constructing and applying outrigger, hook and/or pulley components. For those who are inexperienced in the construction of custom molded splints/braces and in particular the handling and molding of low temperature thermoplastic materials, this system provides a precise custom fitted splint/orthosis requiring fewer construction skills.

A dynamic or static progressive or serial static splint in some embodiments according to the invention can be provided with bases that are readily conformable to the bearing surfaces of the patient's extremities as part of the splint construction process. Some embodiments provide a method of attachment of outriggers that allows simple but precise mounting.

Some embodiments provide means of securing the attachments positively and rapidly. Some embodiments provide a quick and adjustable mechanism to secure the bases to the extremity.

Some embodiments provide a simple and easy to operate system for adjusting mechanisms carried by the outrigger, e.g. providing greater or lesser tension on a finger loop.

DETAILED DESCRIPTION OF EMBODIMENTS ACCORDING TO THE INVENTION

The present invention now will be described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

It will be understood that, when an element is referred to as being "coupled" or "attached" to another element, it can be directly coupled or attached to the other element or intervening elements may be present. In contrast, when an element is referred to as being "directly coupled" to another element, there are no intervening elements present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and should not be interpreted in an idealized or overly formal sense expressly so defined herein.

Some embodiments include a single base or multiple bases. These will be referred to as base components. A splint for a patient may involve one or more bases and hence be referred to as having a base component and second base component or first and second base component.

The base component can be made of various plastic materials known in the art. The plastic materials preferred are base materials made from high temperature thermoplastics as low temperature thermoplastics may deform with time and temperature such as when left in a parked car.

Figure 1A:
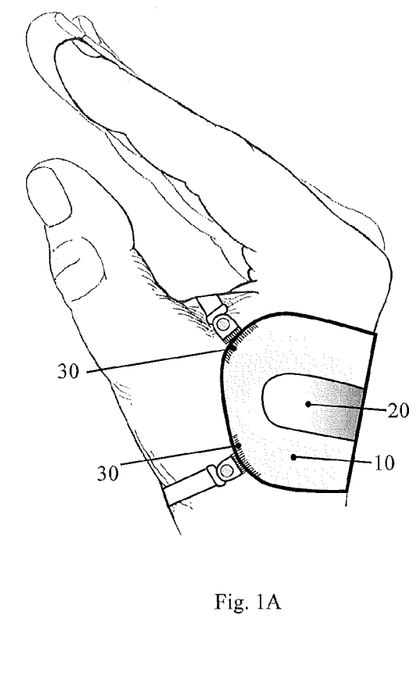
FIGS. 1A-B are perspective views of a base positioned on a patient's arm.
Figure 1B:
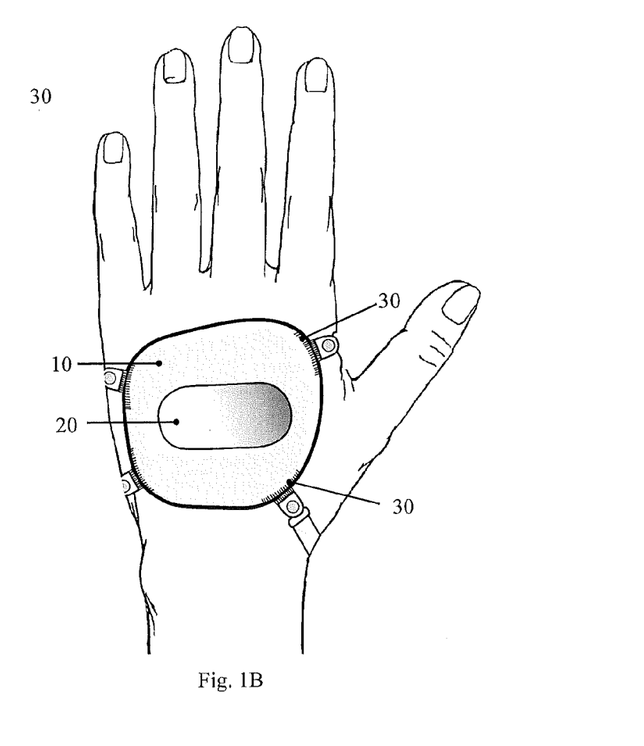

As shown in FIGS. 1A and 1B, the base 10 is preferable plastic with an embedded metal insert 20. This allows the therapist to quickly conform the base to the extremity, e.g. forearm, for comfort and proper bearing support. In some embodiments, a device can include a base form or forms which can be a formed shape with, for example, optional padding material on one or more sides of the formed shape, one or more straps attached, and with or without intervening components. The base may also be supplied with integral slots 30 at approximate locations where mounting straps normally would be attached.

Figure 2:
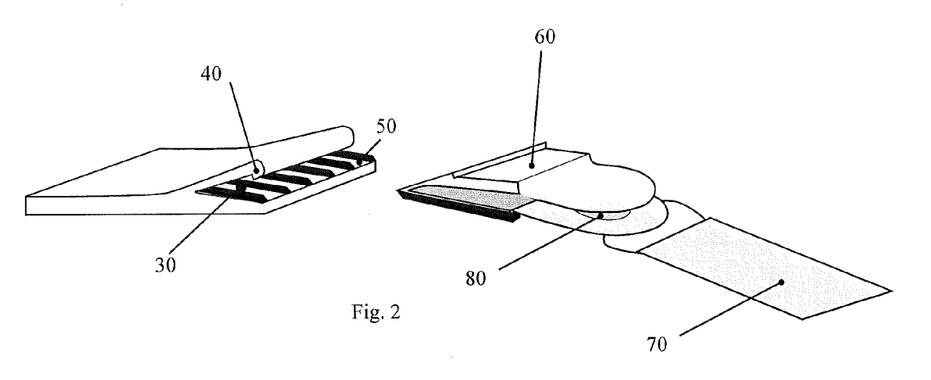
FIG. 2 is a perspective view of a strap locking embodiment.

Referring to FIG. 2, an integral slot 30 is formed at portions of the base's periphery where straps could be expected to be mounted. The slot 30 is contoured 50 on its inside with grooves, ridges, etc. A lip or cusp 40 can be formed on one or both sides of the edge. The contoured surface is to receive a tab 60 that has corresponding contour, e.g. grooves or steps as illustrated. One of ordinary skill can readily appreciate other contours that allow a simple snap fit of the tabs into the groove so as to lock it and prevent easy withdrawal of the tab. Likewise, the molded contour can reduce lateral shifting of the tab within the slot. The straps 70 can be mounted to the tab via a swivel 80 to aid in proper positioning.

The device may also include intervening components used with the base form and/or the outrigger component and/or loop component and/or hooks, pulleys, and hinges components. In some embodiments, the intervening components may be coupled with the base forms. In some embodiments, the intervening components may include arcuate shapes which allow adjustment in one plane. In some embodiments, the intervening components may include components which allow flexibility in one or more planes. In some embodiments, the intervening components may be modular, allowing one or more of the modular pieces to be coupled. In some embodiments, the intervening components may be rigid or may be partially flexible or may be wholly flexible. In some embodiments, the intervening components may have adjustable and/or bendable pieces. In some embodiments, the intervening components may couple with the base forms and other intervening components and/or outrigger components and/or hooks and/or loops and/or pulleys and/or hinges. In some embodiments, the intervening components may include a pre-molded interlocking material or resealable fastener on one or more surfaces; the interlocking material may vary in its means of attachment or may be molded as part of the intervening component.

Figure 4:
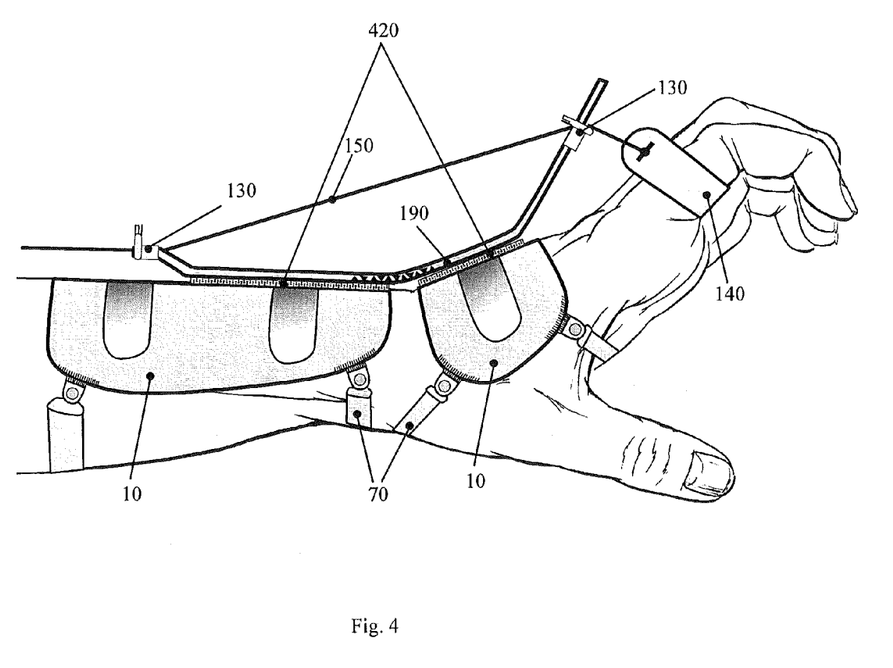
FIG. 4 is a perspective view of multiple bases and an intervening component which is also an outrigger component.

A splint may comprise multiple bases or base components. FIG. 4 illustrates a splint carried by the forearm and hand. Bases 10 are affixed with mounting straps 70. Between the bases is an intervening component 190, here an outrigger. An intervening component which is not an outrigger may also be used between two bases.

An intervening component can also be used to fix the articulation angle of a joint. In such a case, a base is installed on each side of a joint such as shown in FIG. 4. The joint is then positioned to the intended articulation angle. That angle is then fixed by mounting a rigid intervening component to both bases. The rigid nature of the intervening component maintains the fixed angle.

Figure 5:
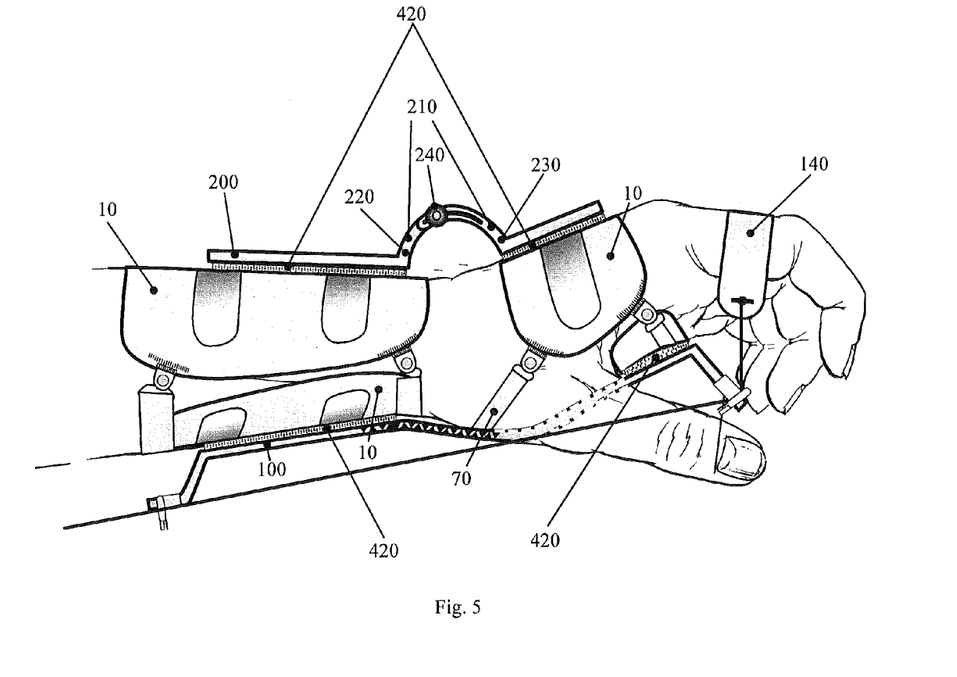
FIG. 5 is a perspective view of multiple bases and an adjustable intervening component and an outrigger.

FIG. 5 illustrates the use of another intervening component 200. The intervening component is a bar with an adjustable arcuate part 210. The intervening component is fixed to base component 10. The adjustable arcuate part may be one arc 230 that tracks within a second arc 220. A fastener such as a set screw 240 may operate to fix the angle of the wrist joint at the appropriate angle. The splint may also include an outrigger 100 that allows for tensioning of a finger loop 140.

In some embodiments, hook, pulley, and/or hinge components may be used. In some embodiments, additional components such as hooks, pulleys, or hinges may be coupled with the base form, the outrigger component, the strapping component and/or the intervening components or used separately. In some embodiments, the hooks, pulleys, and hinges component may also be provided without the base unit to be applied to custom molded bases.

Figure 6:
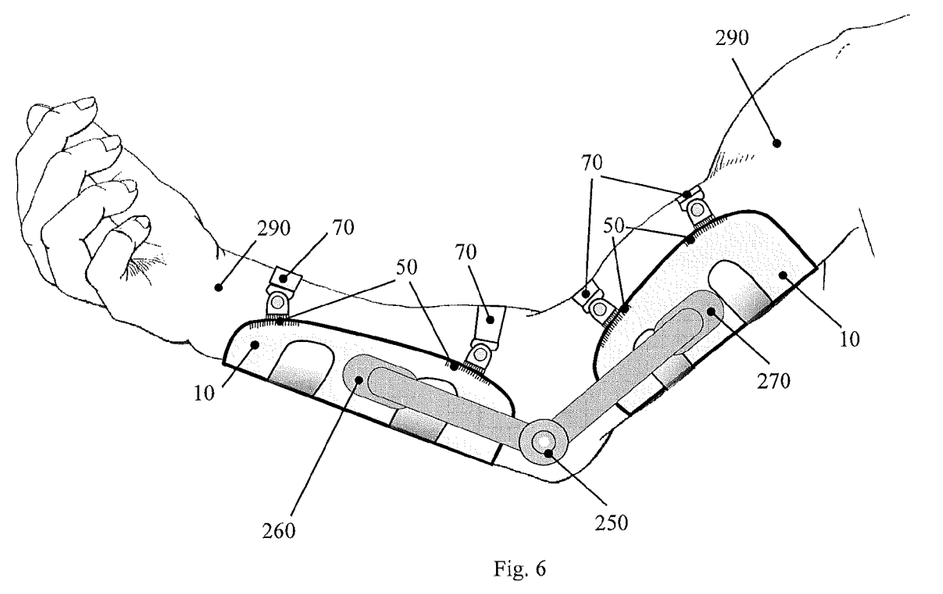
FIG. 6 is a perspective view of the splinting of an arm at a certain elbow angle.
Figure 7A:
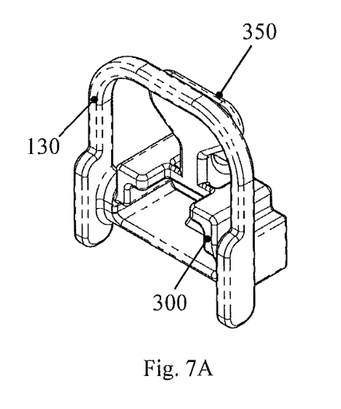
FIGS. 7A-E are views of a guide.
Figure 7B:
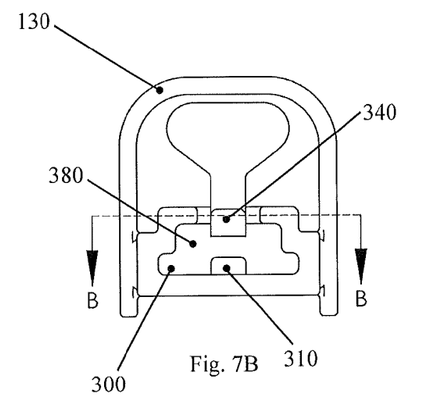
Figure 7C:
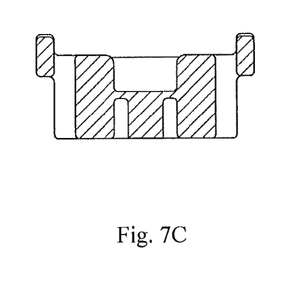
Figure 7D:
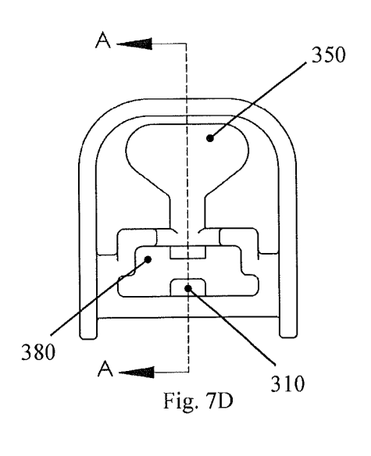
Figure 7E:
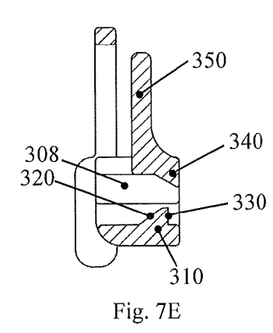

FIG. 6 shows an embodiment where the intervening component is an elbow hinge 250. Bases 10 here are formed to the forearm 280 and upper arm 290. Straps 70 are positioned within preplaced grooves 50 to secure the bases to the arm. The articulable arms 260 and 270 of the hinge are securely mounted to the bases to establish the articulation angle of the elbow. A similar hinge is preferably placed diametrically opposite the elbow on the other side in the same manner (not shown).

Figure 3A:
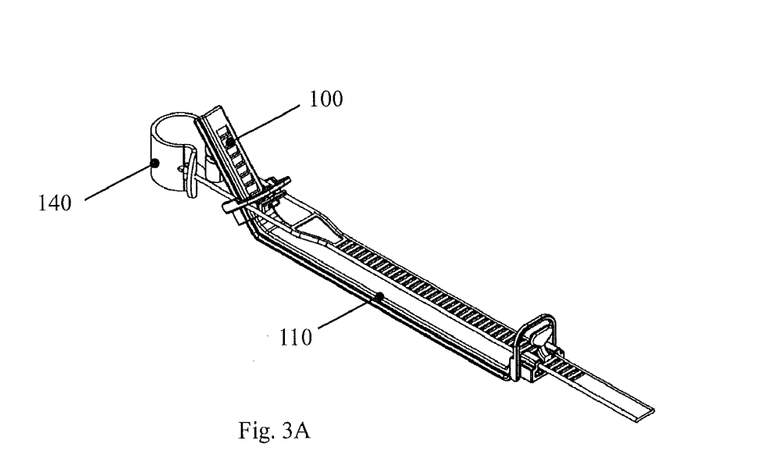
FIGS. 3A-C are views of an outrigger and guides.
Figure 3B:
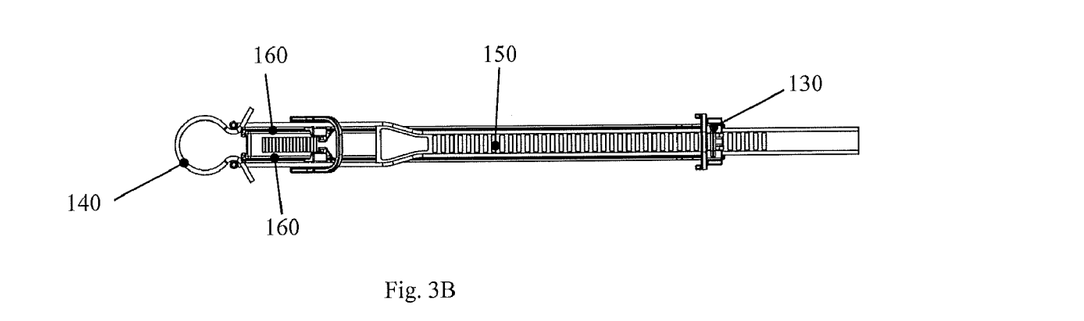
Figure 3C:
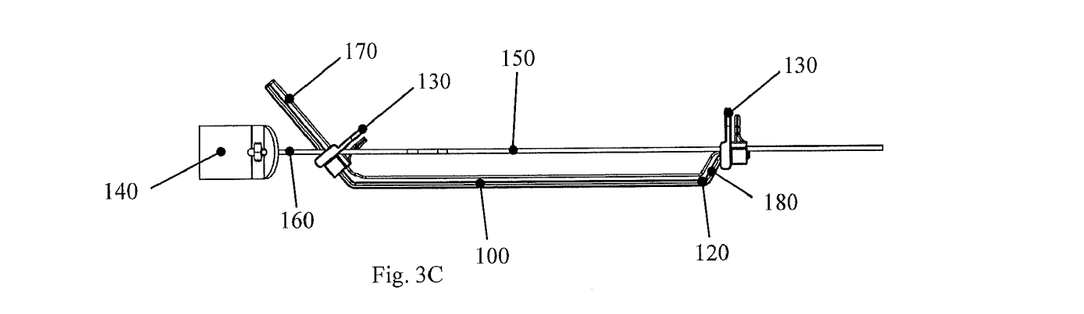

Turning to FIGS. 3A-3C, outriggers are shown for attachment to the base 10. The outrigger comprises a central rail 110. The ends of the rail can be arcuate or curved 120. Carried on the rail can be one or more guides 130. In some embodiments, the central rail is made from injection molded plastic.

In use, the outriggers are attached to the base 10.

The device may also include an outrigger component which can include a preformed shape that includes an adjustable and releasable part at one end and moveable adjustable part at the opposing end with or without intervening elements. The device may also include a loop unit that includes a preformed part at one end which traverses through the adjustable and releasable component of the outrigger on the other end. The loop can include two round linear forms 160 each of which may attach to one side of the loop material 140. Other finger or digit engaging hardware may be used in addition to or without the finger loop. The outrigger may or may not include a molded interlocking or reclosable fastener component on one or more surfaces. In some embodiments, the outrigger and the additional separate parts may vary in application method. In some embodiments, the outrigger may also be provided without the base unit to be applied to custom molded bases. In some embodiments, the loop unit provides either a static or an adjustable static force. In other embodiments, the loop unit may provide elastic force or elastic limited force or elastic adjustable force. In some embodiments, the length and configuration of the loop and outrigger varies.

FIGS. 3A-3B illustrate a outrigger carrying a finger loop or finger support 140. Alternatively or in addition, an outrigger could carry hooks, pulleys, etc. The finger loop 140 is attached to a strip 150 via two round linear extensions of the strip 160. The strip may be threaded through the guide 130 at the distal end of the outrigger 170 and through another guide at the proximal end 180. Alternatively, the strip 150 can integrally contain (such as via one piece molding) the linear extensions 160 and finger loop 140.

FIGS. 7A-E illustrate an embodiment of a guide 130. The guide 130 is slidably mounted on the outrigger by riding on rail flanges that fit in the lower portion of aperture 300. The guide has a lower pawl 310 that fits within notches on the outrigger body. The lower pawl 310 has one side angled 320 so as to allow it to ride over the walls between notches on the outrigger body. Once resting in such a notch, the guide 130 is resistant to movement in the opposite direction due to the squared edge 330.

Figure 8:
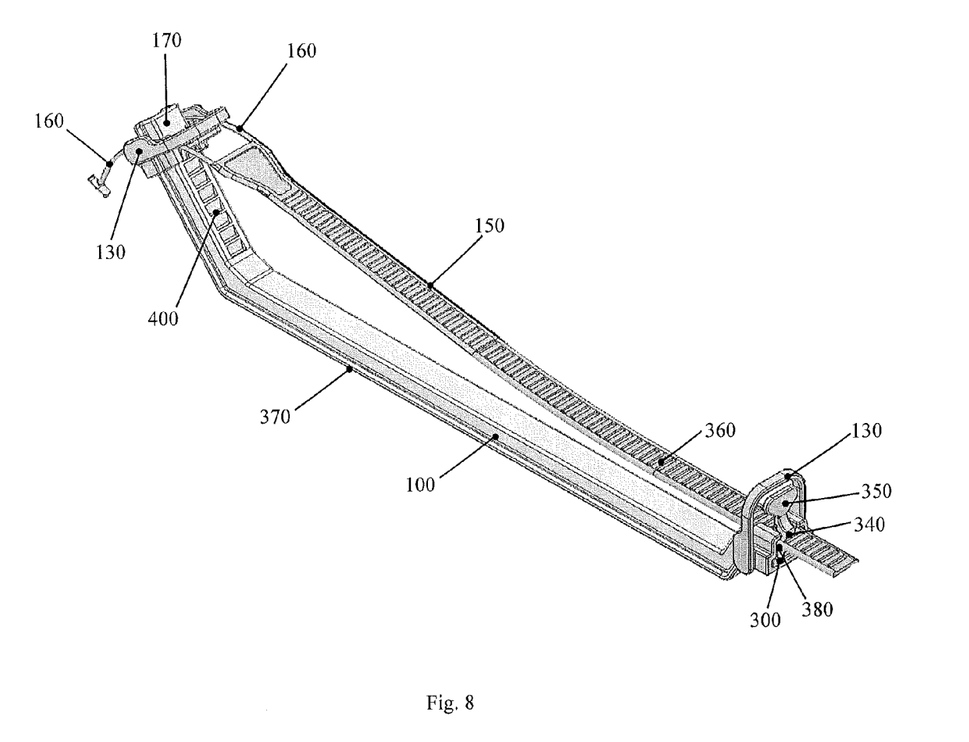
FIG. 8 is a perspective view of an outrigger with tensioning strap.

Turning to FIG. 8, a tensioning strip 150 slidably moves within upper aperture 380 of the guide. Guide 130 also has an upper pawl 340 that fits in one of a series of notches along the length of strips 150. The interaction between upper panel 340 and the notches allow the tensioning strip to be advanced through the guide while resisting movement in the opposite direction. In certain embodiments, the upper pawl 340 may be combined with a release tab 350. Depressing the release tab 350 moves the upper pawl out of the notches of the tension strap allowing it to move in either direction or be removed and replaced with another strip to carry other hardware.

Other variations on the guide 130 can now be apparent to those in the art so as to allow a strip to be guided and secured relative to the outrigger so that static or dynamic forces at the end of the strap connected to the patient (e.g. at the finger) can be distributed to the outrigger. Likewise, the guide and the outrigger need not require the shape of the strip shown but may e.g. utilize a cable of a rounded cross section or other mechanisms to adjustably attach the patient contacting hardware, e.g. 140, to the outrigger and bear the forces there between. There may also be an intervening elastic or adjustable elastic component.

FIG. 8 illustrates one embodiment of the outrigger. The guides ride on lateral flanges 370 on either side of outrigger 100. Those flanges are slidable within the lower aperture 300 of the guide 130. Two guides 130 mounted on the outrigger carry the tension strip 150. The strip rides within the upper aperture 380 of the guide 130. The strip 150 has notches 360 along its length to interact with the upper pawl 340. Adjustment of tension strip 150 to exert more tension on the hardware mounted on the distal end involves moving the strip proximally through a series of notches, usually resulting in an audible click for each notch.

The distal guide 130 is slidable over the distal portion 170 of the outrigger 100. The guide has the round linear extensions 160 at the distal portion of the strip 150. The assembly is constrained within the guide. The guide is placed along the distal portion of the outrigger to achieve the desired angle of the linear extensions 160 and hence the distal hardware, e.g. finger loop 140, to the outrigger. The upper pawl 340 of the guide resides in the notches 400 to maintain the position of the guide 130 on the outrigger 100.

In some embodiments, the base form, outrigger component, strapping component, intervening components and/or the hooks, pulleys and hinges components attach to any other component with a formed interlocking material which engages with a formed interlocking material on the opposing surface. In some embodiments, the pre-molded interlocking material may be applied with self-adhesive. In some embodiments, the formed interlocking material may be molded as an integral part of the molded base form, outrigger component, strapping component, intervening components and/or the hooks, pulleys, and hinges components. In some embodiments, a moldable substance may be imbedded between the formed interlocking surfaces which may be self-hardening. In some embodiments, a moldable substance may be imbedded between the formed interlocking surfaces which may be plaster of Paris or another moldable substance which can harden.

Outriggers, intervening components, and other hardware may be attached to the bases by reclosable fasteners 410. Hook and loop fasteners may be used where the mounting on the base is repeatedly redone. Hook and loop fasteners may not provide sufficient shear support to maintain the alignment of parts relative to the base or may allow excessive movement.

Figure 9A:
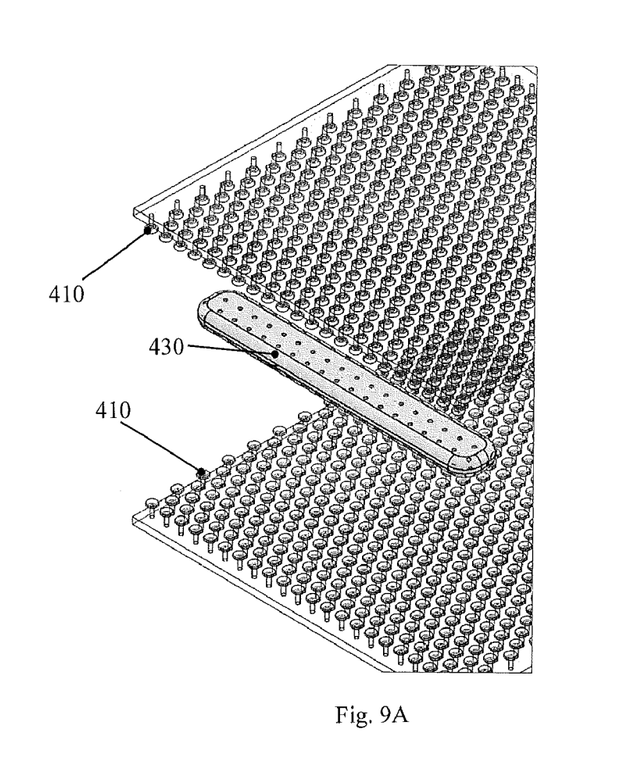
FIGS. 9A-C are views of a resealable fastener including a locking adhesive.
Figure 9B:
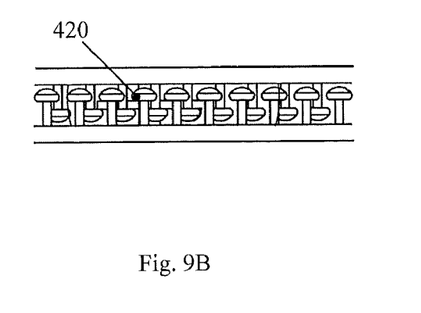
Figure 9C:
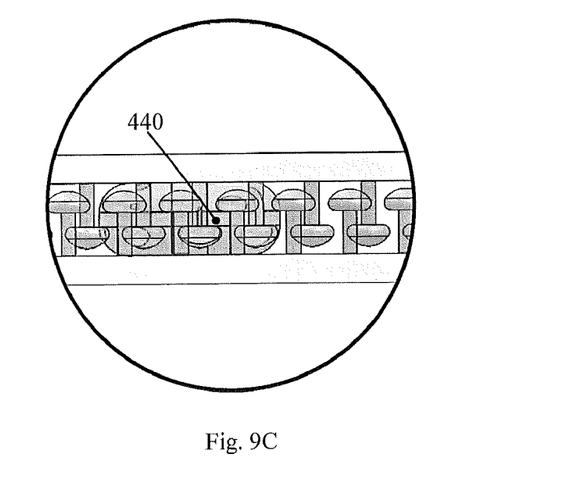

Since the parts will be removed or repositioned a limited number of times, a reclosable fastener such as 3M Dual Lock reclosable fastener is preferred. FIGS. 9A-C show an example of a reclosable fastener. This type of fastener uses opposed "mushrooms" that interlock 420 with audible snaps when pressed together. Each set of opposing mushrooms can be carried by an adhesive tape or one side may be pre-molded with the relevant component. In practice, a strip of adhesive tape would be mounted on the underside of hardware such as the outrigger 100 or intervening component. The other tape would be adhered to the base 10. The therapist could reposition the parts relative to one another until the desired location is achieved. The reclosable fastener could also be pre-molded on the base, especially at locations most likely to be used.

While these fasteners have sufficient shear resistance, in some applications their peel strength may cause concern for a piece of hardware coming loose. Larger more rigid reclosable fasteners may be used. Alternatively or in addition, the bond can have increased resistance to removal by use of an adhesive to lock the projections in their interlocked location. Once the therapist has achieved the desired position of the components, an adhesive 430 such as epoxy can be applied to one or both surfaces of projecting connectors. The epoxy or moldable substance may be in liquid, gel or putty forms to allow conformance and penetration with reduced runoff. The hardware is then mounted by pressing the hardware into place with the projections interlocking and the adhesive surrounding the interlocked projection 440. While an example is epoxy, other adhesives or fillers can be used where they have sufficient rigidity and body to fill the gaps around the fasteners and after curing or hardening prevent the fasteners from deforming in response to tensile forces. The adhesive or putty can also be used to fill in gaps where two pieces are not conforming, e.g. a flat outrigger on a curved based.

In some embodiments, the device (including, for example, the base form, the outrigger and the finger loop unit, the intervening components, and the strap components) can be provided as a kit which may be assembled according to the particular needs of a subject. For example, the base form may be applied to either right or left extremity and may be applied across one or more joints. In some embodiments, the device may be available as dedicated to the right or left extremity. In some embodiments, the outrigger components (including strip 150), intervening components, strap components and/or loop components may be applied to custom molded bases.

EXAMPLE

This example goes through the basic application of a splint according to the present inventions.

I. Select and Apply Base Components
   A. Measure the circumference of the appropriate anatomical area (metacarpal, forearm, etc) and choose the appropriate sized base component.
   B. Apply the component to the area as illustrated. If there is both a dorsal and volar component for the anatomic area, apply both components simultaneously.
   C. Tighten/adjust all strap closures to assure the base component is secure.
   D. Bend the base component to fit the underlying anatomical shape and/or modify edges as needed to relieve pressure or adjust fit.

II. Position and Connect Base Components Using Intervening Components, if Applicable
   For some uses, base components may be applied both distal and proximal to a joint. To position the joint between the base components, intervening components are attached to the distal and proximal base components.
   A. Attachment
      1. Identify the desired location of the intervening component and mark this location lightly with a pencil on the base form.
      2. Cut to the size marked the pre-molded interlocking material with self-adhesive backing.
      3. Attach the self-adhesive pre-molded interlocking material firmly to the base.
      4. Attach the matching pre-molded interlocking material which is part of the intervening component to the pre-applied interlocking material on the base.
      5. NOTE: If rigid stability is required or desired (especially if force will be applied across the joint) imbed the adhesive substance between the formed interlocking surfaces when applying the intervening component. After the joint has been correctly positioned, allow the adhesive to cure.
   B. Joint Positioning
      1. Some intervening components have adjustable/movable parts which allow the joint position to be adjusted. Move the adjustable parts until the desired joint position is obtained and lock the adjustable part in place.
      2. Manually test for stability of the base components in relation to one another. If increased stability is required:
         i. Imbed the adhesive substance between the formed interlocking surfaces when applying the intervening component. After the joint has been correctly positioned, allow the adhesive to cure.
      AND/OR
         ii. Apply an intervening component on the opposite side of the extremity following the instructions above.
      3. Be sure to maximally secure the base components and the intervening components before proceeding further.

III. Apply Hinge Components, if Applicable
   For some uses, base components may be applied both distal and proximal to a joint and the intervening components are hinges which allow but may restrict movement of the intervening joint.
   A. Attachment
      1. Identify the desired location of the hinge component and mark this location lightly with a pencil on both the proximal and distal base forms.
      2. Cut to the size marked the pre-molded interlocking material with a self-adhesive backing.
      3. Attach the pre-molded interlocking material firmly to the base.
      4. Attach the matching pre-molded interlocking material which is part of the hinge component to the pre-applied interlocking material on the base.
      5. NOTE: If rigid stability is required (especially if force will be applied across the joint) imbed the adhesive substance between the formed interlocking surfaces when applying. After the joint has been correctly positioned, allow the adhesive to cure.
      6. Apply a hinge component on the opposite side of the joint in the identical manner, if desired.
   B. Hinge Stop
      1. If restriction of the movement of the joint is desired, set the stop on the hinge at the desired number of degrees of joint movement.

IV. Apply Outrigger, Hook, and/or Pulley Components, if Applicable
  A. Outrigger Components
    1. Joints not restricted by the base component may have force applied via an outrigger component. This component attaches to the base component.
    2. Identify the desired location of the outrigger component and mark this location lightly with a pencil on the base form.
    3. Cut to the size the pre-molded interlocking material with a self-adhesive backing to adhere to the area marked on the base.
    4. Attach the pre-molded interlocking material firmly to the base.
    5. Attach the matching pre-molded interlocking material on the outrigger component to the pre-applied interlocking material on the base.
    6. Evaluate the position of the outrigger component to assure it is properly positioned for an effective line of pull.
    7. NOTE: If rigid stability is required (especially if force will be applied across the joint) imbed the adhesive substance between the formed interlocking surfaces when applying or after precise location has been determined. After the outrigger has been correctly positioned, allow to cure.
    8. After outrigger is securely applied, adjust the distal part of the outrigger to provide the line of pull desired. As joint motion improves, adjust the line of pull to maintain the desired angle.
  B. Hook and/or Pulley Components
    1. Joints not restricted by the base component may be controlled via a hook or pulley component as known in the art. This component attaches to the base component.
    2. Identify the desired location of the hook or pulley component and mark this location lightly with a pencil on the base form.
    3. Cut to the size the pre-molded interlocking material with a self-adhesive backing to adhere to the area marked on the base.
    4. Attach the interlocking material firmly to the base.
    5. Attach the matching pre-molded interlocking material on the hook or pulley component to the pre-applied interlocking material on the base.
    6. Evaluate the position of the hook or pulley component to assure it is properly positioned.
    7. Apply a loop unit, if appropriate, for the desired function.
    8. NOTE: If rigid stability is required (especially if force will be applied across the joint) imbed adhesive between the formed interlocking surfaces when applying. After the outrigger has been correctly positioned, allow the epoxy to cure.

That which is claimed is:

1. A splint for positioning joints of an arm and/or hand comprising:
    a base configured to mount on the arm and/or hand;
    mounting straps coupled to the base that are configured to secure the base on the arm and/or hand;
    an outrigger mounted on the base, wherein the outrigger includes:
        a body;
        a first guide mounted on a first end of the body;
        a second guide slidably mounted on an opposite, second end of the body to allow slidable movement of a point of connection of the second guide to the second end of the body; and
    a tensioning strip extending between the first and second guides that is configured to couple to finger hardware configured to engage a finger on the hand, wherein the tensioning strip is adjustably movable in the first guide to apply a selected tension to the finger hardware.

2. The splint of claim 1 further comprising pre-positioned textured slots in said base for attaching said mounting straps.

3. The splint of claim 1 wherein said outrigger is mounted on said base by a high shear strength reclosable fastener.

4. The splint of claim 3 further comprising:
    a second base, separate from the first base, for mounting to said arm and/or hand across a joint on the arm and/or hand from said base; and
    an intervening component, separate from the outrigger, adapted to be secured to said base and second base spanning said joint and establishing an articulation angle for said joint, wherein said intervening component is adapted to be secured to said base and second base by a second reclosable fastener.

5. The splint of claim 4 wherein said intervening component is a hinge.

6. The splint of claim 5 wherein said hinge comprises an adjustable articulation mechanism that can be locked at a selected angle.

7. The splint of claim 1, wherein the base comprises a first base and a separate second base and wherein the first and second base are configured to mount on the arm and/or hand with a joint of the arm and/or hand between the first and second base and wherein the outrigger comprises an intervening component that couples the first base to the second base and establishes an articulation angle therebetween.

8. The splint of claim 1, wherein the base comprises a first base and a separate second base and wherein the first and second base are configured to mount on the arm and/or hand with a joint of the arm and/or hand between the first and second base and wherein the splint further comprises an intervening component that couples the first base to the second base and establishes an articulation angle therebetween.

9. The splint of claim 1, wherein the base comprises a plastically deformable material that may be molded to the arm and/or hand.

10. A splint for positioning joints of an arm and/or hand comprising:
    a base configured to mount on the arm and/or hand;
    mounting straps coupled to the base that are configured to secure the base on the arm and/or hand;
    an outrigger mounted on the base, wherein the outrigger includes:
        a body;
        a first guide mounted on a first end of the body;
        a second guide slidably mounted on an opposite, second end of the body,
    wherein said outrigger is mounted on said base by a high shear strength reclosable fastener;
    a tensioning strip extending between the first and second guides that is configured to couple to finger hardware configured to engage a finger on the hand, wherein the tensioning strip is adjustably movable in at least one of the first or second guides to apply a selected tension to the finger hardware; and
    adhesive to lock the reclosable fastener in a closed state with the outrigger mounted on the base.

11. A splint for positioning joints of an arm and/or hand comprising:
- a base configured to mount on the arm and/or hand;
- mounting straps coupled to the base that are configured to secure the base on the arm and/or hand,
- an outrigger mounted on the base, wherein the outrigger includes:
  - a body,
  - a first guide mounted on a first end of the body,
  - a second guide slidably mounted on an opposite, second end of the body; and
- a tensioning strip extending between the first and second guides that is configured to couple to finger hardware configured to engage a finger on the hand, wherein the tensioning strip is adjustably movable in at least one of the first or second guides to apply a selected tension to the finger hardware, wherein the body of the outrigger comprises a rail and wherein the rail includes an angled portion at the second end thereof and wherein the second end receives an end of the tensioning strip that is configured to couple to the finger hardware.

12. The splint of claim 11, wherein the tensioning strip is adjustably movable in the first guide and wherein the second guide comprises an angle adjuster guide slidably mounted on the angled portion of the rail to adjust an angle of the tensioning strip extending between the first and second guides.

* * * * *

UNITED STATES PATENT AND TRADEMARK OFFICE
CERTIFICATE OF CORRECTION

PATENT NO. : 8,337,441 B2  
APPLICATION NO. : 12/868156  
DATED : December 25, 2012  
INVENTOR(S) : Judy C. Colditz Page 1 of 1

It is certified that error appears in the above-identified patent and that said Letters Patent is hereby corrected as shown below:

In the Specification:
Column 2, Line 65: Please begin a new paragraph at "Some embodiments…"

Column 3, Line 2: Please begin a new paragraph at "Some embodiments…"

Column 7, Line 5: Please correct "opposed "mushrooms" that interlock"
to read -- opposed "mushrooms" 410 that interlock --

Signed and Sealed this
Eleventh Day of March, 2014

Michelle K. Lee
*Deputy Director of the United States Patent and Trademark Office*